United States Patent
Watanabe

[11] Patent Number: 5,889,140
[45] Date of Patent: Mar. 30, 1999

[54] CROSS-LINKABLE OR CURABLE POLYLACTONE COMPOSITION, CROSS-LINKED OR CURED MOLDING MADE THEREFROM AND PROCESS FOR THE PRODUCTION THEREOF

[75] Inventor: Kazushi Watanabe, Otake, Japan

[73] Assignee: Daicel Chemical Industries, Ltd., Tokyo, Japan

[21] Appl. No.: 809,060
[22] PCT Filed: Jul. 10, 1996
[86] PCT No.: PCT/JP96/01920
§ 371 Date: Mar. 10, 1997
§ 102(e) Date: Mar. 10, 1997
[87] PCT Pub. No.: WO97/03130
PCT Pub. Date: Jan. 30, 1997

[30] Foreign Application Priority Data

Jul. 10, 1995 [JP] Japan ................................... 7-196974
Jul. 10, 1995 [JP] Japan ................................... 7-196975

[51] Int. Cl.$^6$ .................................................. C08G 63/08
[52] U.S. Cl. .............................. 528/354; 528/75; 528/80; 528/81; 528/492; 528/503; 522/75; 522/79; 522/90; 522/134; 264/45.1; 264/77; 264/236
[58] Field of Search ................................ 528/354, 75, 80, 528/81, 492, 503; 522/75, 79, 90, 134; 264/50, 45.1, 77, 236

[56] References Cited

U.S. PATENT DOCUMENTS 4,629,779 12/1986 Koleske .
4,725,653 2/1988 Koleske .

FOREIGN PATENT DOCUMENTS 60-120716 6/1985 Japan .
60-215018 10/1985 Japan .
61-241354 10/1986 Japan .
5-279445 10/1993 Japan .

*Primary Examiner*—Duc Truong
*Attorney, Agent, or Firm*—Morgan & Finnegan, LLP

[57] ABSTRACT

A crosslinkable polylactone-based composition comprising formulating 100 parts by weight of a polylactone (A) whose number average molecular weight is in the range of 10,000 to 300,000 and 0.1 to 30 parts by weight of a crosslinkable monomer (B) which can confine the molecular chain of the polylactone (A) by irradiating active energy radiation or by heating, a production method of a polylactone-based crosslinked molded article prepared by irradiating active energy radiation or by heating after melting and molding the above-mentioned crosslinkable polylactone-based composition at the temperature where crosslinking does not occur, and a polylactone-based crosslinked molded article obtained by the above method are offered. A cured polylactone-based molded article having similar properties is also obtained from the curable polylactone-based composition composed of a polylactone or polylactone composition (X) comprising a prescribed polylactone (C) and polyvalent alcohol (D), and a prescribed curing agent (Y).

Since these molded articles obtained have biodegradability as well as excellent mechanical strength, thermal resistance, oil resistance, abrasion resistance, and shape-memorizable property which is a property to deform showing rubber elasticity on applying an external force when it is heated to soften and to tend to recover its initial shape of the molded article when it is reheated to soften, the product can be used for a sheet for fixing a patient in radiation therapy, a material for transcribing a shape of wig, a material for transcribing a shape of teeth, and gypsum.

26 Claims, 1 Drawing Sheet

CROSS-LINKABLE OR CURABLE POLYLACTONE COMPOSITION, CROSS-LINKED OR CURED MOLDING MADE THEREFROM AND PROCESS FOR THE PRODUCTION THEREOF

TECHNICAL FIELD

The present invention relates to a crosslinkable or curable-type polylactone-based composition, a polylactone-based crosslinked or cured molded article therefrom, and its production method and applications.

The polylactone-based crosslinked or cured molded article offered by the present invention has biodegradability as well as excellent physical properties such as mechanical properties, thermal resistance, oil resistance and abrasion resistance, and shape-memorizable property that while an article deforms showing rubber elasticity on applying an external force when it is heated to soften, and it keeps the deformed shape when it is cooled as it is deformed to solidify, it tends to recover its initial shape when it is reheated to soften. Thus, various uses applying these properties are offered.

BACKGROUND ART

Japanese Patent Publication (Kokai) No. 279445/1993 describes that a film-form molded product, a fiber or the like of a polycaprolactone composition containing a small amount of urethane bonds can be produced by melt blending a polyvalent isocyanate of 0.1 to 5% parts by weight to a polycaprolactone of 100 parts by weight.

Japanese Patent Publication (Kokai) No. 279445/1993 describes that since the presence of gel may cause problems such as fish eye, filament break, or reduction of moldability due to plugging by gel in the nozzle, the amount of polyisocyanate added must be less than 5 parts by weight to a polycaprolactone of 100 parts by weight. Such publicly-known conventional techniques have failed to offer molded products in which polylactone is crosslinked or cured, but considered only partial improvement, for instance, improvement of melt tensile strength by reacting the terminated-hydroxyl group of polylactone with a small amount of isocyanate. Accordingly, a polylactone with rubber elasticity in softened state by heating or shape memorizable property on a satisfactory level has not been obtained, and naturally application development requiring such new functions has not been made yet.

DISCLOSURE OF THE INVENTION

As a result of the intense study on the above-mentioned subjects, namely, (1) to obtain a polylactone-based molded article with rubber elasticity in softened state by heating and shape-memorizable property on a satisfactory level, and (2) to establish a production method of the above-mentioned polylactone molded article, the present inventors have found that a polylactone-based crosslinked molded article with the above-mentioned functions could be obtained by confining a polylactone chain through the crosslinking structure formed by using a polylactone (A) whose number average molecular weight is in the range of 10,000 to 300,000 and a specific crosslinkable monomer (B) and found a production method of molded articles such as sheet, film, fiber, tray, bottle, bag, etc. The degree of confinement of the polylactone molecular chain can be expressed in terms of later-mentioned "recovery ratio" expressing the shape-memorizable property of the polylactone-based crosslinked molded article to be obtained, and the "confinement in the present invention means the recovery ratio of 80% or higher.

Further, as a result of the intense study on the cured polylactone, the present inventors also found that a cured polylactone-based molded article of sheet, bottle, film, etc. which has excellent physical properties such as mechanical properties, thermal resistance, oil resistance and abrasion resistance as well as shape-memorizable property could be obtained by molding a curable polylactone-based composition formulated with a specific curing agent of various types that can react with a hydroxyl group in a specific lactone-based composition to complete the present invention.

Namely, according to a first aspect of the present invention, there is provided a crosslinkable polylactone-based composition comprising 100 parts by weight of a polylactone (A) whose number average molecular weight is in the range of 10,000 to 300,000 formulated with 0.1 to 30 parts by weight of a crosslinkable monomer (B) that can confine a molecular chain of polylactone (A) on irradiating active energy radiation or on heating.

According to a second aspect of the present invention, there is provided a production method of a polylactone-based crosslinked molded article characterized by crosslinking by irradiating active energy radiation or by heating after melting and molding at a temperature where crosslinking of the above-mentioned polylactone-based composition will not occur.

Further, according to a third aspect of the present invention, there is provided a polylactone-based crosslinked molded article obtained by the above description.

Furthermore, according to a fourth aspect of the present invention, there is provided various applications of the above-mentioned polylactone-based crosslinked molded article, for example, a sheet for fixing a patient in radiation therapy, a material for transcribing a shape of wig, a material for transcribing a shape of teeth, a gypsum and a biodegradable disposable type molded article.

According to a fifth aspect of the present invention, there is provided a curable polylactone-based composition comprising a polylactone or polylactone composition (X) composed of 20 to 100% by weight of a polylactone (C) whose number average molecular weight is in the range of 10,000 to 200,000 and hydroxyl group moles per 1 g are in the range of $1\times10^{-5}$ to $5\times10^{-4}$ and 0 to 80% by weight of polyvalent alcohol (D) whose number average molecular weight is less than 10,000 (The total of (C) and (D) is 100% by weight), and one or more curing agent(s) (Y) selected from polyfunctional isocyanates, polyfunctional epoxides, polyfunctional carboxylic acids and melamine compounds.

According to a sixth aspect of the present invention, there is provided the production method of a cured polylactone-based molded article characterized by molding a curable polylactone-based composition in the fifth aspect of the invention in the temperature range of 100°–250° C. or by postheating at 100° to 2500° C. after molding.

According to a seventh aspect of the present invention, there is provided a cured polylactone-based molded product obtained by the above description, especially a cured polylactone-based molded article whose content of the chloroform-insoluble components is over 30% by weight.

According to an eighth aspect of the present invention, there is provided various applications of the above-mentioned cured polylactone-based molded article, for example, a sheet for fixing a patient in radiation therapy, a material for transcribing a shape of wig, a material for transcribing a shape of teeth, a gypsum and a biodegradable disposable type molded article.

BEST MODE OF THE EMBODIMENT OF THE INVENTION

[1] In the following, a crosslinkable polylactone-based composition, a polylactone-based crosslinked molded article, and their applications are explained.

The polylactone (A) used for a crosslinkable polylactone-based composition in the present invention is obtained by publicly-known methods to polymerize by ring-opening addition of a lactone monomer with a compound having an active hydrogen like alcohol called initiator. Here, the initiator may be any compound that has a hydroxyl group, an amino group, a thiol group, etc. in the molecule without any limitations, but generally an alcoholic compound is used. The specific examples of the above-mentioned alcoholic compound include aliphatic alcohols such as methanol, ethanol, and butanol, glycols such as ethylene glycol, diethylene glycol, 1,4-butandiol, 1,6-hexanediol, and neopentyl glycol, and polyvalent alcohols such as trimethylol propane, trimethylol ethane, glycerine, and pentaerythritol.

The above-mentioned lactone monomer can include all the lactone compounds that are cyclic ester compounds, specifically, for example, ε-caprolactone, methylated lactones such as 4-methyl caprolactone, δ-valerolactone, methylated valerolactone, β-propiolactone, butyrolactone, and their mixtures.

The number average molecular weight of the polylactone (A) produced from the above-mentioned initiator and lactone monomer as the raw materials and used in the present invention is in the range of 10,000 to 300,000, preferably 40,000 to 200,000, more preferably 60,000 to 150,000. The molecular weight of lower than 10,000 will make it difficult to produce a variety-crosslinked molded article as an object of the present invention and the mechanical properties will be very low even if produced. The molecular weight of higher than 300,000 will make the melt viscosity so high that the processability is unpreferably retarded.

The crosslinkable monomer (B) in the present invention has no limitation if it can be formulated and mixed in polylactone and crosslink the polylactone by irradiation of active energy ray or heating. Such a crosslinkable monomer (B) can be composed of one kind of compound, or a mixture of two or more compounds. The crosslinkable monomer (B) is formulated and mixed solely or optionally with appropriate initiator, catalyst, stabilizer, etc.

The specific examples of the crosslinkable monomer (B) include a polyfunctional acrylic monomer ($B_1$), any mixed monomer ($B_2$) of a polyfunctional isocyanate and a polyfunctional alcohol, any mixed monomer ($B_3$) of a polyfunctional isocyanate and a polyfunctional amine, a polyfunctional allyl-based monomer, any mixed monomer of a polyfunctional epoxy and a polyfunctional carboxylic acid or a polyfunctional amine, any mixed monomer of melamine and polyfunctional alcohol or formaldehyde.

A polyfunctional acrylic monomer is a compound that has more than one (meth)acryloyl groups, specifically, ethylene oxide (EO)-modified bisphenol A di(meth)acrylate, 1,4-butanediol di(meth)acrylate, diethylene glycol di(meth)acrylate, dipentaerythritol hexa(meth)acrylate, dipentaerythritol monohydroxy penta(meth)acrylate, caprolactone modified dipentaerythritol hexa(meth)acrylate, pentaerythritol tri(meth)acrylate, pentaerythritol tetra(meth)acrylate, polyethylene glycol di(meth)acrylate, trimethylolpropane tri (meth)acrylate, EO-modified trimethylolpropane tri(meth) acrylate, propylene oxide (PO)-modified trimethylolpropane tri(meth)acrylate, tris(acryloxyethyl)isocyanurate, tris (methacryloxyethyl)isocyanurate and their mixtures in general. Especially, tris(acryloxyethyl)isocyanurate, namely, triacrylic acid ester of tris(2-hydroxyethyl)isocyanuric acid is low skin irritant and favorably used.

Here, (meth)acrylate means either acrylate or methacrylate.

The polyfunctional isocyanate is a compound that contains more than one isocyanate groups, specifically, hydrocarbon diisocyanate (e.g. alkylene diisocyanate, arylene diisocyanate, and cycloaliphatic diisocyanate) and publicly-known triisocyanate and polymethylene poly(phenylene isocyanate) are exemplified. As preferred diisocyanates, 1,2-diisocyanate ethane, 1,4-diisocyanate butane, 2,4-diisocyanate toluene (2,4-TDI), 2,6-diisocyanate toluene (2,6-TDI), 3,5-diisocyanate-o-xylene, 4,6-diisocyanate-m-xylene, 2,6-diisocyanate-p-xylene, 2,4-diisocyanate-1-chlorobenzene, 2,4-diisocyanate-1-nitrobenzene, 2,5-diisocyanate-1-nitrobenzene, 4,4'-diphenylmethane diisocyanate (MDI), 2,4'-diphenylmethane diisocyanate, 3,3'-diphenylmethane diisocyanate, isophorone diisocyanate, cyclohexane diisocyanate, cyclohexane diisocyanate, hydrogenated MDI, polymeric MDI, polymethylene poly(phenylene isocyanate) and isocyanurates of these and mixtures of the above-mentioned substances are exemplified, especially, the mixture of 80% by weight of 2,4-diisocyanate toluene and 20% by weight of 2,6-diisocyanate toluene ("TDI 80/20"), mixture of 80% by weight of TDI 80/20 and 20% by weight of polymeric polymethylene (polyphenylene isocyanate), and isocyanurate which is the cyclic trimer of the above-mentioned isocyanate are used.

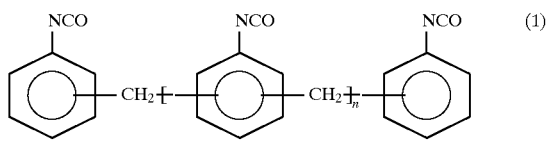

(wherein n is in the range of 0 to 2)

As the polyfunctional alcohols that can be used with a polyfunctional isocyanate or melamine, ethyleneglycol, diethyleneglycol, propyleneglycol, 1,4-butanediol, neopentylglycol, 1,6-hexanediol, cyclohexanedimethanol, trimethylolethane, trimethylolpropane, glycerin, pentaerythritol, ditrimethylolpropane and their mixtures are exemplified.

As the polyfunctional amines that can be used with a polyfunctional isocyanate or a polyfunctional epoxy, ethylenediamine, diethylene triamine, triethylene tetramine, ethylene oxide modified diethylene triamine, ethylene oxide modified triethylene tetramine, diethylaminopropyl amine, metaphenylene diamine, diamino diphenylmethane, diamino diphenylsulfone and their mixtures are exemplified.

As the polyfunctional allyl monomers, triallyl cyanurate, triallyl isocyanurate, diallyl phthalate, diallyl benzene phosphonate and their mixtures are exemplified.

As the polyfunctional epoxy, which are compounds having more than one epoxy groups, various polymers containing as a radical polymerization component an epoxy compound having radical polymerizability such as glycidyl (meth)acrylate, epoxidized elastomer made by epoxidizing double bonds in an elastomer, diepoxy compounds such as glycidyl ether and a publicly-known epoxy resin are given.

More specifically, glycidyl methacrylate-modified polyethylene (Lexpearl) by Nippon Oil Co., Ltd., glycidyl methacrylate-styrene copolymer (Marploop) glycidyl methacrylate modified styrene-butadiene copolymer by Nihon Yushi Ltd Corp., bisphenol A/epichlorhydrin-type epoxy resin (Epikote) by Yuka-Shell Epoxy, bisphenol A/epichlorhydrin-type epoxy resin (Araldite) by Ciba-Geigy, and compounds containing cycloaliphatic epoxy group(s) in the molecule, for example, 3,4-epoxy cyclohexylmethyl-3',4'-epoxy cylcohexane carboxylate [Celloxide 2021 by Daicel Chemical Ind.] denoted by the formula below (2), lactone-modified product of the same denoted by the formula (3), further, cycloaliphatic and triepoxide denoted by the formulas (4) and (5), cycloaliphatic tetraepoxide by the formula (6), respectively, further, cycloaliphatic epoxy resin having the structure in which a unit having either of epoxy/vinyl/ester group as the side chain of the cyclohexane ring is connected by an ether linkage [EHPE-3150, etc. by Daicel Chemical Ind.], and modified epoxy resin made by modifying epoxy resin having the secondary hydroxyl groups such as Araldite 6097, 6084 and 6071 with lactone to form the primary hydroxyl groups [Placcel G by Daicel Chemical Ind./Disclosed in Japanese Patent Unexamined Publication No. 1607/1987] are exemplified. Here, $n1$, $n2$, $n3$ and $n4$ in formulas (5) and (6) are all intergers of 0 or 10.

(2)

(3)

[wherein b is an integer. Celloxide 2080 by Daicel Chemical Ind.]

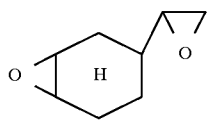

(4)

[Celloxide 3000 by Daicel Chemical Ind.]

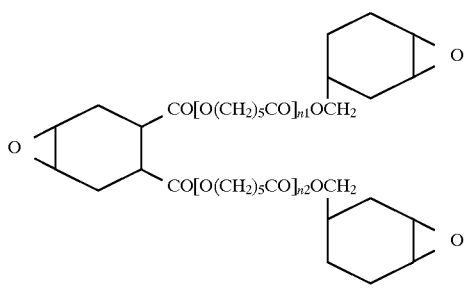

(5)

[Cycloaliphatic epoxy resin, Epolead GT-300 by Daicel Chemical Ind.]

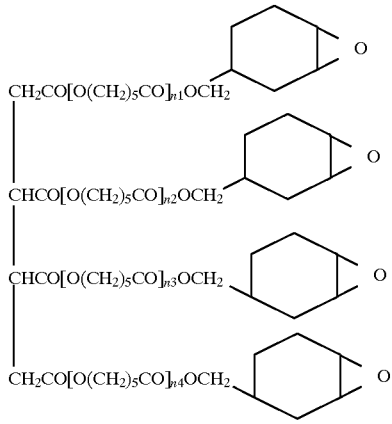

(6)

[Cycloaliphatic epoxy resin, Epolead GT-400 by Daicel Chemical Ind.]

As the polyfunctional carboxylic acids used with a polyfunctional epoxide, polyvalent carboxylic acid derivatives such as polyvalent carboxylic acids and polyvalent carboxylic anhydrides and polymers having these polyvalent carboxylic acids in the skelton are exemplified, specifically, dibasic acids such as terephthalic acid, phthalic acid, maleic acid, succinic acid, adipic acid, and anhydrides of these, trivalent carboxylic acids such as benzene tricarboxylic acid, cyclohexane tricarboxylic acid, naphthalene tricarboxylic acid, hexane tricarboxylic acid and anhydrides of these, and polymers modified with various polyvalent carboxylic acids such as pyromellitic anhydride, styrene-maleic anhydride copolymer, acrylic acid copolymerized acrylic resin, and maleic anhydride modified polyolefin elastomer are exemplified.

As the melamine compounds, though mainly melamine is directly used, an oligomer made by partly condensing melamine and polyvalent alcohol can be used as a melamine compound.

As initiators, catalysts, and stabilizers optionally blended with the crosslinkable monomer (B), for example, when UV is used as the active energy ray, photoinitiators, photoinitiation promotors and photosensitizers such as acetophenone-, benzoin-, benzophenone-, and thioxanthone-derivatives; in case of thermal radical polymerization, radical initiators such as peroxides and azobisisobutyl nitrile (AIBN), and polymerization inhibitors such as phenolic or thioether derivatives; in case of reaction between polyfunctional isocyanate and polyfunctional alcohol, tin-based catalysts such as dibutyl tin dilaurate; in case of polyfunctional epoxy and polyfunctional carboxylic acid, catalysts such as tertiary amines and imidazol are exemplified.

The production method of a polylactone-based crosslinked molded article in the present invention has no particular limitations, and is typically exemplified by the following method: To 100 parts by weight of the polylactone (A), 0.1 to 30 parts by weight, preferably 0.2 to 20 parts by weight, more preferably 0.3 to 10 parts by weight of the crosslinkable monomer (B) is formulated, melt blended at a temperature at which no crosslinking occurs to produce a crosslinkable polylactone based composition, formed into various molded products such as a sheet, film, fiber, tray, bottle or bag, then crosslinked by the crosslinkable monomer (B) contained in the composition by irradiating active energy ray or by heating.

In the case that formulated amount of the above-mentioned crosslinkable monomer (B) is less than 0.1% by weight, it is not sufficient to confine the molecular chain of polylactone (A), so the rubber elasticity when various molded articles obtained by crosslinking in the above are reheated to soften or the property to recover the previous shape of the molded product (shape-memorizable property) when various molded products obtained by crosslinking in the same way are reheated to soften, deformed, cooled, and again reheated to soften is not on a satisfactory level, and reversely the amount over 30% by weight tends to unpreferably give too much rigidity and too low toughness.

The melt mixer or molding machine used for producing crosslinkable polylactone composition can be any publicly-known device without problems. For example, as a melt mixer, an extruder, kneader, roll, mixer, etc., and as a molding machine, extruder, compression molding machine, vacuum molding machine, blow molding machine, T-die molding machine, injection molding machine, inflation molding machine, etc. can be exemplified.

In the melt mixer or molding machine the mixture treating temperature must be a temperature at which crosslinking does not occur, and is normally lower than 100° C., preferably not less than 50° C. and lower than 100° C.

As specific examples of the active energy radiation to produce a polylactone-based crosslinked molded product, ultraviolet ray (UV) and electron beam (EB) may be given and publicly-known equipment may be used without problems. The range of 100 to 5,000 kV is suitable as the accelerating voltage of electron beam (EB) and so is 0.1 to 30 NRad as the radiation dose.

When the polylactone is crosslinked with crosslinkable monomer by heating, the heating is made at the temperature range of 100° to 250° C. preferably 120° to 250° C., more preferably 180° to 200° C. after fixing the molded product by placing on a support or holding with a holder so that the molded product obtained by heating will not deform.

At a temperature lower than 100° C. the crosslinking reaction hardly occur or the reaction rate is so low that a long time is necessary to complete, and at a temperature higher than 250° C. the polylactone-based crosslinked product in the present invention unpreferably discolors or is degraded. The crosslinking reaction time is in the range of 0.5 to 30 minutes, preferably 1 to 20 minutes, more preferably 2 to 15 minutes, and when the reaction time is shorter than 0.5 minutes the crosslinking reaction is insufficient, and reversely when the time is longer than 30 minutes, it is unnecessarily long, consuming meaningless time.

The polylactone-based crosslinked article in the present invention is formed from the polylactone (A) and the crosslinkable monomer (B) and other substances may be incorporated without problems at a suitable time depending on the application.

As the above-mentioned substances inorganic fillers such as glass fiber, glass beads, metal powder, talc, mica, and silica, pigments, additives such as various stabilizers, flame retardants, antistatic agents, antifungal agents, plasticizers, and viscosity enhancer, thermoplastic resins and curable oligomers are exemplified.

A polylactone-based crosslinked molded article obtained by the present invention is obtained by crosslinking a composition mainly containing the polylactone by active energy radiation or by heating, and the molded product shows biodegradability as well as various excellent properties such as mechanical strength, thermal resistance, oil resistance, and abrasion resistance, furthermore so-called shape-memorizable property that while an article deforms showing rubber elasticity on applying an external force when it is heated at 40° to 100° C. to a softened state, and keeps the deformed shape when it is cooled to solidify as deformed, it tends to recover the initial shape when it is reheated to soften without an external force. Accordingly, the product can be applied for various applications using these properties. It can be used as a molding material of biodegradable disposable products for many applications, for example, ski boots, wigs, a material for transcribing a shape of teeth, medical materials such as a sheet for fixing a patient to fix the patient head in radiation therapy and a gypsum, products as molded articles that have many chances to be left in natural environment or are difficult to reutilize such as ostomy backs, cut dressing agents, bandages, diapers, sanitary napkins, tampons, paper diapers, raw waste bags, excrete bags, urea bags, laundry bags, medical waste containers, agricultural films, construction sheets to fix land slope to prevent soil falling down in road construction and the like, various containers used in army, pesticides and fertilizer bottles and bags, and packaging films to prevent from scratches and damages in medium and large size overseas exported products and the like.

The application method of the shape-memorizable property will be explained, taking as an example in gypsum and a sheet for fixing a patient in radiation therapy. To take an accurate and precise mold of the affected part or to tightly fix the patient head, a sheet of polylactone-based crosslinkable molded product is heated to soften to apply on a face, where it is often required to correct the form by heating the defective part only to locally shrink when the softening time is so short that the sheet is cooled down to solidify without good contact or is overstretched. In these cases, the purpose is easily attained by reheating the sheet locally utilizing the property to recover its initial shape.

Taking an example of a material for transcribing a shape of teeth, a piece of the sheet of the polylactone-based molded product with sufficient thickness for mold making is heated to soften, e.g. at 60° C., and inserted between teeth, bitten and cooled down to transcribe the tooth shape. If necessary, the mold of tooth shape is reheated to soften to recover the shape of the sheet piece before the tooth shape is transcribed, which enables use of the piece for transcribing a shape of teetn again by reheating to soften.

The shape-memorizable property in the present invention can be expressed by the recovering ratio measured by the method shown in the following examples, and a value of higher than 80% is preferable, in particular, 90% is more preferable.

[2] The curable polylactone composition, cured polylactone-based molded article, and their production methods of the present invention are described.

The cured polylactone-based molded product of the present invention is obtained by preparing a curable polylactone-based composition from a polylactone or polylactone composition (X) composed of polylactone (C) and polyvalent alcohol (D), and a curing agent (Y) and reacting hydroxyl groups existing in polylactone or polylactone composition (X) and curing agent (Y) by the heat in molding.

The above-mentioned polylactone (C) is a straight chain or radial polylactone whose number average molecular weight is in the range of 10,000 to 200,000 and hydrogen group mole number per 1 g is in the range of $1 \times 10^{-5}$ to $5 \times 10^{-4}$ moles. The production method of the above-mentioned polylactone is publicly-known, for example, the polylactone is obtained by ring-opening addition polymerization of a lacton monomer with compound having active hydrogen such as alcohol called initiator. Here, the initiator is a compound with hydroxyl group, amino group, thiol group and the like without limitations, but an alcoholic compound is generally used.

As specific examples of the above-mentioned alcoholic compounds, aliphatic alcohols such as methanol, ethanol, and butanol, glycols such as ethylene glycol, diethylene glycol, 1,4-butanediol, 1,6-hexanediol, neopentyl glycol, and polyvalent alcohols such as trimethylol propane, trimethylol ethane, and glycerine pentaerythritol are exemplified. Above all, as the preferable initiators used in the present invention, various glycols, 3–4 functional alcohols such as trimethylol propane and pentaerythritol and their mixtures are exemplified. The reason is that the use of the polylactone produced with the above-mentioned initiator facilitates to control the crosslinking structure such as the distance between crosslinking points and the crosslinking density within a suitable range to obtain excellent properties of a cured polylactone-based molded article in the present invention.

The above-mentioned lactone can include all lactone compounds as cyclic ester compounds, specifically, ε-caprolactone, methylated caprolactone such as 4-methyl caprolactone, δ-valerolactone, methylated valerolactone, βpropiolactone and butyrolactone and their mixtures are given as the examples.

The number average molecular weight of the polylactone (C) used in the present invention is in the range of 10,000 to 200,000, preferably 20,000 to 150,000, more preferably 40,000 to 100,000. When above-mentioned the number average molecular weight is less than 10,000, the mechanical strength such as tearing strength and tensile strength of the cured polylactone-based molded product in the present invention decreases, and when the number average molecular weight is over 200,000, the hydroxyl group concentration of the polylactone (C) decreases and reduce the reactivity with the curing agent (Y) to unpreferably retard sufficient curing.

The hydroxyl group moles per 1 g of the polylactone (C) is in the range of $1 \times 10^{-5}$ to $5 \times 10^{-4}$ moles, preferably $2 \times 10^{-5} \times 10^{-4}$ moles, more preferably $5 \times 10^{-5}$ to $2 \times 10^{-4}$ moles. When the above-mentioned value is less than $1 \times 10^{-5}$ moles, sufficient curing reaction is unpreferably retarded, and when it is over $5 \times 10^{-4}$ moles, the mechanical properties such as tearing strength and tensile elongation unpreferably deteriorate.

The polyvalent alcohol (D) whose number average molecular weight is less than 10,000 in the present invention has no limitation, and specifically ethylene glycol, diethylene glycol, 1,4-butanediol, neopentyl glycol, trimethylol propane, pentaerythritol, or oligomers which are addition polymerized thereon with cyclic ether such as lactone monomers, ethylene oxide or tetrahydrofurane. The above-mentioned polyvalent alcohol (D) is added to increase the crosslinking density of the curing-type polylactone-based molded article in the present invention, and the number average molecular weight over 10,000 renders the addition meaningless for the remarkably lowered effect to increase the crosslinking density.

The polylactone or polylactone composition (X) in the present invention is composed of 20 to 100% by weight of polylactone (C), 0–80% by weight of polyvalent alcohol (The total of both is 100% by weight.), and the percentage of polylactone (C) in the polylactone or polylactone composition (X) is in the range of preferably 60 to 100% by weight, more preferably 70 to 100% by weight. As the percentage of polyvalent alcohol (D) increases, the crosslinking density of the cured polylactone-based molded product in the present invention increases but reversely physical properties such as impact resistance, tensile elongation, moldability, and biodegradability tend to deteriorate, and the percentage of the polyvalent alcohol (D) exceeding 80% by weight remarkably reduces the above-mentioned properties.

The curing agent (Y) in the present invention indicates one or more compounds selected from polyfunctional isocyanates, polyfunctional epoxides, polyfunctional carboxylic acids and melamine compounds.

The polyfunctional isocyanate is a compound having more than one isocyanate groups, specifically hydrocarbon diisocyanate (e.g. alkylene diisocyanates, arylene diisocyanates and cycloaliphatic diisocyanates) and publicly-known triisocyanate and polymethylene poly(phenylene isocyanate) are given. As preferable diisocyanates, 1,2-diisocyanate ethane, 1,4-diisocyanate butane, 2,4-diisocyanate toluene (2,4-TDI), 2,6-diisocyanate toluene (2,6-TDI), 3,5-diisocyanate-o-xylene, 4,6-diisocyanate-m-xylene, 2,6-diisocyanate-p-xylene, 2,4-diisocyanate-1-chlorobenzene, 2,4-isocyanate-1-nitrobenzene, 2,5-diisocyanate-1-nitrobenzene, 4,4'-diphenylmethane diisocyanate (MDI), 2,4'-diphenylmethane diisocyanate, 3,3'-diphenylmethane diisocyanate, isophorone diisocyanate, cyclohexane diisocyanate, hydrogenated MDI, polymeric MDI, polymethylene poly(phenylene isocyanate) and their isocyanurate and mixtures of the above-mentioned substances are given, in particular, the mixture of 80% by weight of 2,4-diisocyanate toluene. and 20% by weight of 2,6-diisocyanate toluene([TDI80/20]), the mixture of 80% by weight of TDI80/20 and 20% by weight of polymerized polymethylene indicated by the following formula (1) (polyphenylene isocyanate), and isocyanurate as a cyclic trimer of the above-mentioned isocyanate are used.

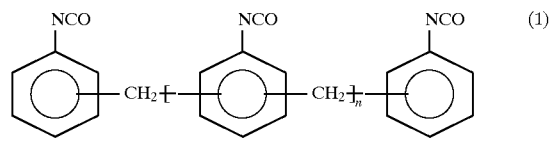

(wherein n is in the range of 0 to 2)

The polyfunctional epoxides are compounds having more than one epoxy groups and include various polymers which contain, as radical polymerizing components, epoxy compounds with radical polymerizability such as glycidyl (meth) acrylate, epoxidized elastomer where double bonds of an elastomer are epoxidized, diepoxy compounds such as glycidyl ether and publicly-known epoxy resin.

More specifically, glycidyl methacrylate modified polyethylene (Lexpearl) by Nippon Oil Co., Ltd., glycidyl methacrylate-styrene copolymer (Marploop) by Nihon Yushi, Ltd. Corp., glycidyl methacrylate-modified styrene-butadiene copolymer, bisphenol A/epichlorohydrin type epoxy resin (Epikote) by Yuka-Shell Epoxy Corp., bisphenol A/epichlorohydrin type epoxy resin (Araldite) by Chiba-Geigy Corp., and compounds having cycloaliphatic epoxy group in the molecule, for example, 3,4-epoxy cyclohexylmethyl-3',4'-epoxy cyclohexane carboxylate as shown in the following formula (2) [Celloxide 2021 and the like by Daicel Chemical Ind. Ltd.], lactone-modified product of the same as shown in the following formula (3), further, cycloaliphatic di- or tri-epoxide as shown in the following formula (4) or (5), cycloaliphatic tetra-epoxide as shown in the following formula (6), cycloaliphatic epoxy resin with a structure in which a unit having either of epoxy/vinyl/ester group as a side chain is connected to the cyclohexane ring with an ether linkage [EHPE-3150 and the like by Daicel Chemical Ind., Ltd.], epoxy resin in which an epoxy resin with a secondary hydroxyl group such as Araldite 6097, 6084 and 6071 is modified with a lactone to a primary hydroxyl group [Placcel G by Daicel Chemical Ind., Ltd./disclosed in Japanese Patent examined Publication No. 1607/1987], etc. can be exemplified. Here, n1, n2, n3 and n4 in the formula (5) and (6) are integers of 0 or 10.

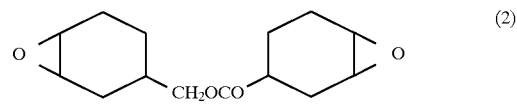

[wherein b is an integer. Celloxide 2080 by Daicel Chemical Ind., Ltd.]

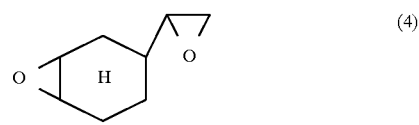

[Celloxide 3000 by Daicel Chemical Ind., Ltd.]

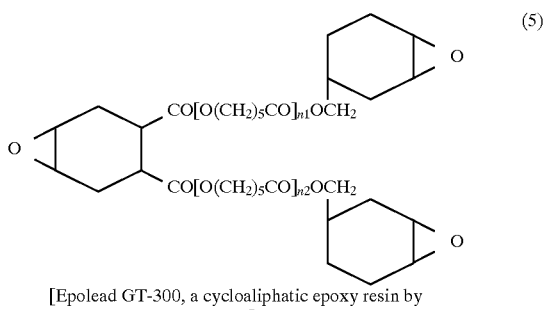

[Epolead GT-300, a cycloaliphatic epoxy resin by Daicel Chemical Ind., Ltd.]

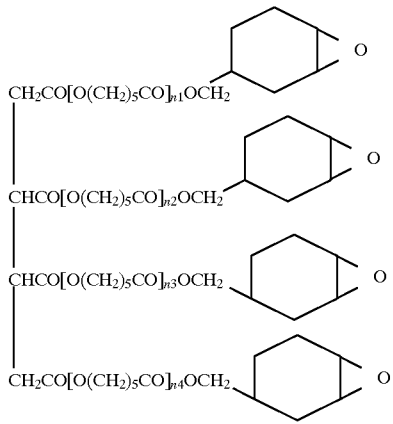

[Epolead GT-400, a cycloaliphatic epoxy resin by Daicel Chemical Ind., Ltd.]

As polyfunctional carboxylic acids, polyvalent carboxylic acids, polycarboxylic acid derivatives such as polycarboxylic anhydrides, and polymers having these polyvalent carboxylic acids in the skeleton, specifically, divalent carboxylic acids such as terephthalic acid, phthalic acid, maleic acid, succinic acid, and adipic acid, and anhydrides of these acids, trivalent carboxylic acids such as benzene tricarboxylic acid, cyclohexane tricarboxylic acid, naphthalene tricarboxylic acid, and hexane tricarboxylic acid, and anhydrides of these acids, pyromeritic anhydride, and various polyfunctional carboxylic acids modified polymers such as styrene-maleic anhydride copolymer, acrylic acid copolymerized acrylic resin, and maleic anhydride modified polyolefin elastomer are exemplified.

As melamine compounds, while melamine is mainly used directly, it is also possible to use an oligomer in which melamine and polyvalent alcohol are partially condensed as a melamine compound.

In the present invention, the properties of the cured polylactone-based molded product obtained are greatly different depending on how much curing agent (Y) is formulated and reacted to the total moles of hydroxyl groups in the polylactone or polylactone composition (X). Normally, however, crosslinking of as high as 10% of the total moles of hydroxyl groups improves various properties such as mechanical strength, thermal resistance, oil resistance, and shape-memorizable property remarkably compared with the uncured product, and increase of the formulated amount of the curing agent (Y) further enhances cure to strengthen the tendency. As cure proceeds, the amount of the gel component insoluble in chloroform (chloroform-insoluble gel content) occupied in the total cured polylactone-based molded article increases. The above-mentioned gel content is normally more than 5% by weight, preferably more than 30% by weight, more preferably more than 50% by weight. Since the chloroform-insoluble gel content in the cured polylactone-based molded product differs depending on the molding temperature to cure (reaction temperature) and time, the formulation quantity of the curing agent (Y) is decided so that the gel content becomes more than 5% by weight.

The measuring method of the chloroform insoluble gel content will be described later.

In the preliminary mixing of the polylactone or polylactone composition (X) and the curing agent (Y) in the present invention, the mixing method and order are not particularly limited. It may be that the polylactone (C) and the polyvalent alcohol (D) are mixed beforehand then the curing agent (Y) is added to prepare the cured polylactone-based composition, or that the polylactone (C), polyvalent alcohol (D) and the curing agent (Y) are mixed at the same time to prepare the cured polylactone-based composition. Normally, either the method that the polylactone (C), the polyvalent alcohol (D) and the curing agent (Y) are melt blended in the temperature range of 60° to less than 100° C. so that no curing occurs using extruder, kneader, static mixer, and the like, or the method that these three components are dry-blended at room temperature to use for molding, is preferably used.

In this preliminary blending, an appropriate amount of a publicly-known reaction catalyst (The use of dibutyl tin laurate for polyfunctional isocyanates and tertiary amines for polyfunctional epoxides and polyfunctional carboxylic acids is general.) can be mixed to accelerate the reaction between hydroxyl group and curing agent in molding.

The curing reaction of the hydroxyl group in the above-mentioned polylactone or polylactone composition (X) with the curing agent (Y) is made in the temperature range of 100° to 250° C., preferably 150° to 220° C., more preferably 180° to 200° C. At temperatures lower than 100° C. the above-mentioned curing reaction hardly proceeds or is so slow that it takes a very long time, and reversely at a temperature over 250° C. the obtained cured polylactone-based molded product unpreferably discolors or degrades. The curing reaction time is in the range of 0.5 to 30 minutes, preferably 1 to 20 minutes, more preferably 2 to 15 minutes. When the time is less than 0.5 minutes, the curing reaction is insufficient, and when the time is over 30 minutes, it unpreferably takes meaningless time longer than necessary.

In molded products such as bottles, bags, and films obtained by blow molding, inflation molding, and T-die method, the above-mentioned curing reaction is accomplished by reheating after molding, since no or partial curing proceeds during molding. In reheating, when mutual melt adhesion is likely to occur like in bags and film, melt adhesion should be avoided by using a teflon sheet or a release paper as a support or by generating gas stream.

While when a molding equipment is such that can accomplish curing reaction by extending molding time as in compression molding and vacuum molding, the cured polylactone-based molded article in the present invention can be obtained by molding, the method to further complete curing by reheating after molding is preferably adopted.

The curing-type polylactone-based molded product obtained by the present invention is composed of a composition that has polylactone as the main component with excellent properties such as biodegradability, mechanical strength, thermal resistance, oil resistance, abrasion resistance, and so-called shape-memorizable property that when an article is heated at 40° to 100° C. to a soft state and applied with an external force, it deforms showing rubber elasticity, but when it is heated again to soften, it tends to recover the initial shape. Accordingly, the product can be used for various applications, utilizing these properties. Ski boots, wigs, material for transcribing a shape of teeth, a medical material such as a sheet for fixing a patient in radiation therapy to fix the patient head and gypsum, products as molded articles with many chances of leaving in natural environment or of difficult reutilization such as ostomy back, cut dressing agent, bandages, diapers, sanitary napkins, tampons, paper diapers, raw waste bags, excrete bags, urea bags, laundry bags, medical waste containers, agricultural films, construction sheets to fix land slope to prevent soil falling down in road construction and the like, various containers used in army, pesticides and fertilizer bottles and bags, and packaging films to prevent from scratches and damages in medium and large size overseas exported products and the like.

The application method of the shape-memorizable property will be explained, taking as examples in a gyprum and a sheet for fixing a patient in radiation sheet. To take an accurate and precise mold of the affected part or to tightly fix the patient head, the sheet of polylactone-based crosslinked molded product is heated to soften to apply on a face, where only the defective part is often required to heat to locally shrink when the softening time is so short that the sheet is cooled down to solidify without good contact or is overstretched. In these cases, the purpose is easily attained by reheating the sheet locally utilizing the property to recover the original shape.

Taking an example in a material for transcribing a shape of teeth, a piece of the sheet of the polylactone-based molded product with sufficient thickness for mold making is heated to soften, e.g. at 60° C., and inserted between teeth, bitten and cooled down to transcibe the tooth shape. The mold of tooth shape is optionally reheated to soften to recover the shape of the sheet piece before the tooth shape is transcribed, which enables use of the piece for transcribing a shape of teeth again by reheating to soften.

The shape-memorizable property in the present invention can be expressed by the recovering ratio measured by the method shown in the following examples, and a value over 10% is preferable, in particular, over 40% is more preferable.

The present invention will be explained more specifically by examples in the following part, but the invention is not limited by these examples.

[EXAMPLES 1 TO 5]

As polylactone (A), caprolactone ("PCL-H7" by Daicel Chemical Ind., Ltd., a number average molecular weight: 100,000), as crosslinkable monomer (B), isophorone diisocyanate-based isocyanurate ("T1890/100" by Huels A. G.) and trimethylol propane are formulated with the formulation ratio shown in Table 1, and melt blended for 5 minutes at 70° C. with "Labo Plastomill Mixer" by Toyo Seiki Co., Ltd.

The obtained composition was pressed while heating for 20 minutes at 180° C. with a press machine to produce a sheet of 20 mm thickness as a polylactone-based crosslinked molded product. The appearance in softened state, rubber elasticity aspect in softened state, and tensile properties at 60° C. according to JIS K6301 (tensile elongation less than 500%) of the sheet were measured. The results are also given in Table 1. The sheet was cut into 5 mm×4 cm size and elongated by 100% (total length: 8 cm) after softening, then reheated to 60° C. to soften and the extent of recovery % was measured and recorded in Table 1 as the recovery ratio.

[COMPARATIVE EXAMPLES 1 TO 3]

For comparison, sheets were prepared from the sole PCL-H7 used in Examples 1 to 5 or its formulations without trimethylol propane by the same procedure, and the properties were measured. The results are given in Table 1.

[EXAMPLES 6 TO 9]

PCL-H7 as the polylactone (A) and ethylene oxide-modified trimethylol propane ("TMPEOTA" by Daicel-UCB) as the crosslinkable monomer (B) were formulated in the ratio described in Table 2, and melt blended at 70° C. for 5 minutes. The obtained composition was heated and pressed for 10 minutes at 180° C. with press machine to produce a sheet of 2 mm thickness.

At this stage the crosslinking reaction has not occurred yet. On both sides of the sheet electron beam was irradiated under the condition of 200 kV acceleration voltage and 10 NRad radiation dose and the properties were measured as in Example 1. The results are shown in Table 2. For comparison, electron beam irradiation was made for the case without TMPEOTA (Comparative example 4) and the case with TMPEOTA of 35 parts by weight (Comparative example 5) under the same condition, and the properties were measured in the same way. The results are given in Table 2.

TABLE 1

|  | Example | | | | | Comp. Example | | |
|---|---|---|---|---|---|---|---|---|
|  | 1 | 2 | 3 | 4 | 5 | 1 | 2 | 3 |
| Composition | | | | | | | | |
| PCL H7 | 100 | 100 | 100 | 100 | 100 | 100 | 100 | 100 |
| T1890/100 | 1 | 3 | 5 | 7.5 | 10 | 0 | 3 | 7.50 |
| Trimethylolpropane | 0.18 | 0.54 | 0.9 | 1.35 | 1.8 | 0 | 0 | 0 |
| Property | | | | | | | | |
| Appearance in melting*[1] | ○ | ○ | ○ | ○ | ○ | ○ | x | x |
| Rubber elasticity*[2] | Y | Y | Y | Y | Y | N | Y*[3] | Y |
| Tensile strength(kg/cm$^2$) | 0.3 | 0.5 | 0.6 | 0.9 | 1.0 | 0.1 | 2.7 | 1.4 |
| Elongation at break(%) | >500 | >500 | >500 | >500 | >500 | 200 | >500 | 400 |
| Recovery ratio(approx. %) | 80 | 100 | 100 | 100 | 100 | 0 | 90 | 20 |

*[1]:Homogeneity (presence or absence of gel) of the melt sheet was shown in ○ or x, which is the same in the following tables.
*[2]:Sheet was pulled with fingers to see the rubber elasticity and Y denotes presence of rubber elasticity and N denotes absence in the table, which is the same in the following tables.
*[3]:In Comparative example 2, though the recovery ratio was about 90%, gel was seen and the recovery was not uniform in the sheet.

TABLE 2

|  | Example | | | | Comp. Example | |
| --- | --- | --- | --- | --- | --- | --- |
|  | 6 | 7 | 8 | 9 | 4 | 5 |
| Composition |  |  |  |  |  |  |
| PCL H7 | 100 | 100 | 100 | 100 | 100 | 100 |
| TMPEOTA | 0.5 | 1 | 2 | 4 | 0 | 35 |
| Property |  |  |  |  |  |  |
| Appearance in melting | ○ | ○ | ○ | ○ | ○ | x |
| Rubber elasticity | Y | Y | Y | Y | N | Y |
| Tensile strength (kg/cm$^2$) | 0.3 | 0.4 | 0.5 | 0.7 | 0.1 | 10.5 |
| Elongation at break (%) | >500 | >500 | >500 | >500 | 200 | 400 |
| Recovery ratio (approx. %) | 100 | 100 | 100 | 100 | 0 | 50 |

[Boidegradability Test]

The biodegradability of the sheets obtained in the above-mentioned Examples 7, 9 and Comparative example 4 was measured with the sludge of Himeji City Sewage Treatment based on JIS K6950. The results are shown in FIG. 1.

FIG. 1 shows plots of the degradation percentage on ordinate against the testing period (in days up to 28 days) on abscissa. Testing was made twice for the sheets of Example 7 ((a) and (b) in the Figure) and Example 9 ((c) and (d) in the Figure), and once for the sheet of Comparative example 4 ((e) in the Figure). As seen from FIG. 1 the polylactone-based crosslinked molded product in the present invention has improved mechanical strength and thermal resistance, and the biodegradability is only a little inferior to the polylactone itself as comparison in spite of the given shape-memorizable property, which indicates sufficient biodegradability even when it is left in natural environment.

[EXAMPLES 10 TO 19, COMPARATIVE EXAMPLE 6]

As the polylactone (A), caprolactone ("PCL-H7" by Daicel Chemical Ind., Ltd., a number average molecular weight: 100,000 and "PCL-H5" by the same manufacturer, a number average molecular weight: 50,000), as the crosslinkable monomer (B), tris(acryloxyethyl)isocyanurate ("Fancryl EA-731A" by Hitachi Chemical Co., Ltd.) and as nucleating agent, fine silica ("Aerosil #200" by Nippon Aerosil Co., Ltd.) are blended in the formulation ratios shown in Table 3, and melt blended at 100° C. resin temperature with a twin-screw extruder to make pellets.

The obtained pellets were dried at 40° C. for 5 hours, molded with a T-die extruder into sheet of 1.9 mm thickness. At this stage the crosslinking reaction had not occurred yet.

Ten sheets of the sheet were stacked and irradiated with electron beam under the condition of 5,000 kV accelerating voltage and 2 MRad radiation dose. Physical properties of the irradiated sheets were measured as in Example 1. Each of the ten sheets had similar properties. Average properties of the ten sheets are given in Table 3.

As Comparative example 6, a formulation without the crosslinkable monomer (B) were melt blended, molded into sheet, and irradiated with electron beam by the same procedures and the physical properties were measured in the same manner. The results are given in Table 3.

TABLE 3

|  | Example | | | | | | | | | | Comp. Example |
| --- | --- | --- | --- | --- | --- | --- | --- | --- | --- | --- | --- |
|  | 10 | 11 | 12 | 13 | 14 | 15 | 16 | 17 | 18 | 19 | 6 |
| PCL H7 | 30 | 30 | 30 | 30 | 30 | 70 | 70 | 70 | 70 | 70 | 30 |
| PCL H5 | 70 | 70 | 70 | 70 | 70 | 30 | 30 | 30 | 30 | 30 | 70 |
| Fancryl FA-731A | 1.8 | 2.8 | 3.3 | 4.0 | 5.0 | 1.0 | 1.3 | 1.5 | 1.7 | 2.0 | — |
| Aerosil | 0.3 | 0.3 | 0.3 | 0.3 | 0.3 | 0.1 | 0.1 | 0.1 | 0.1 | 0.1 | 0.3 |
| properties |  |  |  |  |  |  |  |  |  |  |  |
| Appearance in melting | ○ | ○ | ○ | ○ | ○ | ○ | ○ | ○ | ○ | ○ | ○ |
| Rubber elasticity | Y | Y | Y | Y | Y | Y | Y | Y | Y | Y | N |
| Tensile strength (kg/cm$^2$) | 0.2 | 0.4 | 0.6 | 0.7 | 2.0 | 0.3 | 0.4 | 0.4 | 0.4 | 0.5 | 0.1 |
| Elongation at break (%) | >500 | >500 | >500 | >500 | >500 | >500 | >500 | >500 | >500 | >500 | 200 |
| Recovery ratio (approx. %) | 100 | 100 | 100 | 100 | 100 | 100 | 100 | 100 | 100 | 100 | 0 |

* Y denotes presence, and N denotes absence.

[EXAMPLES 21 TO 25]

In the ratios shown in Table 4, "PCL H4" (a polycaprolactone by Daicel Chemical Ind., Ltd., a number average molecular weight being 40,000 and hydroxyl group moles per 1 g being 5×10$^{-5}$ moles) as the polylactone (C), "PCL 312" (a trifunctional polycaprolactone by Daicel Chemical Ind., a number average molecular weight being 1,200, and hydroxyl group moles per 1 g of the trifunctional polycaprolactone being 2.5×10$^{-3}$ moles) as the polyvalent alcohol (D), and isophorone diisocyanate (IPDI)-type isocyanurate "T1890/100" (by Huels A. G.) were mixed at 70° C. for 3 minutes with "Labo Plastomill Mixer" by Toyo Seiki Co., Ltd.

Here, the IPDI-type isocyanurate was used in the form of pulverized fine powder and uniformly dispersed into the polycaprolactone without melting. The mixed resin composition was cut into pellets, and pressed at 180° C. for 30 minutes with a compression molding machine "K825" by Kotaki Corp. After cooling a 20 cm×20 cm×2 mm sheet was taken out. Strip form sheets of 1 cm×5 cm (2 mm thickness)

were cut out from the obtained sheet, and the following evaluat0ion was made and the results are given in Table 4.

TABLE 4

|  | Example | | | | | Comp. Example |
| --- | --- | --- | --- | --- | --- | --- |
|  | 21 | 22 | 23 | 24 | 25 | 7 |
| PCL H4 | 100 | 100 | 96 | 90 | 80 | 100 |
| PCL 312 | — | — | 4 | 10 | 20 | — |
| IPDI-type isocyanate | 1 | 5 | 5 | 8 | 12 | — |
| Gellation level (wt %) | 16 | 47 | 83 | 95 | 98 | 0 |
| Recovery ratio (%) | 60 | 100 | 100 | 100 | broken | 0 |

[EXAMPLE 26 TO 28]

In the ratios shown in Table 5, a polycaprolactone using trimethylol propane as an initiator (a number average molecular weight being 85,000 and hydroxyl group moles per 1 g being $3.5 \times 10^{-5}$ moles) as the polylactone (C), a polyfunctional epoxy "Epolead GT-300" (a cycloaliphatic epoxy resin by Daicel Chemical Ind.) as a curing agent, and succinic anhydride as a polyfunctional carboxylic acid were mixed at 70° C. for 3 minutes with "Labo Plastomill Mixer" by Toyo Seiki Co., Ltd. Then, the same procedures as in Example 21 to 25 were made, strip sheets were prepared, evaluation was made, and the results are given in Table 5.

TABLE 5

|  | Example | | | Comp. Example |
| --- | --- | --- | --- | --- |
|  | 26 | 27 | 28 | 8 |
| Polycaprolactone | 95 | 90 | 80 | 100 |
| Epolead GT300 | 1.5 | 5 | 15 | — |
| Succinic anhydride | 0.3 | 1 | 3 | — |
| Gellation level (wt %) | 35 | 90 | 99 | 0 |
| Recovery ratio (%) | 85 | 100 | 100 | 0 |

[COMPARATIVE EXAMPLES 7, 8]

For comparison, "PCL H4" used in Example 21 to 25 and Example 26 to 28 and the caprolactone using trimethylolpropane as an initiator were molded into sheets, respectively, without using the curing agent (Y), and evaluated as in the above-mentioned Examples. Both had gellation level of 0% and showed no shape recovery.

Industrial Applicability

Since the polylactone-based crosslinked molded article offered by the present invention has biodegradability as well as excellent mechanical strength, thermal resistance, oil resistance, abrasion resistance, and shape-memorizable property, the product can be applied for medical materials and various products which have many chances to be left in natural environment or are difficult products to reuse.

Since the crosslinkable-type polylactone-based molded product offered by the present invention has biodegradability as well as excellent mechanical strength, thermal resistance, oil resistance, abrasion resistance, and shape-memorizable property, the product can be applied for medical materials and various disposable-type molded products which have many chances to be left in natural environment or are difficult products to reuse.

Figure 1:
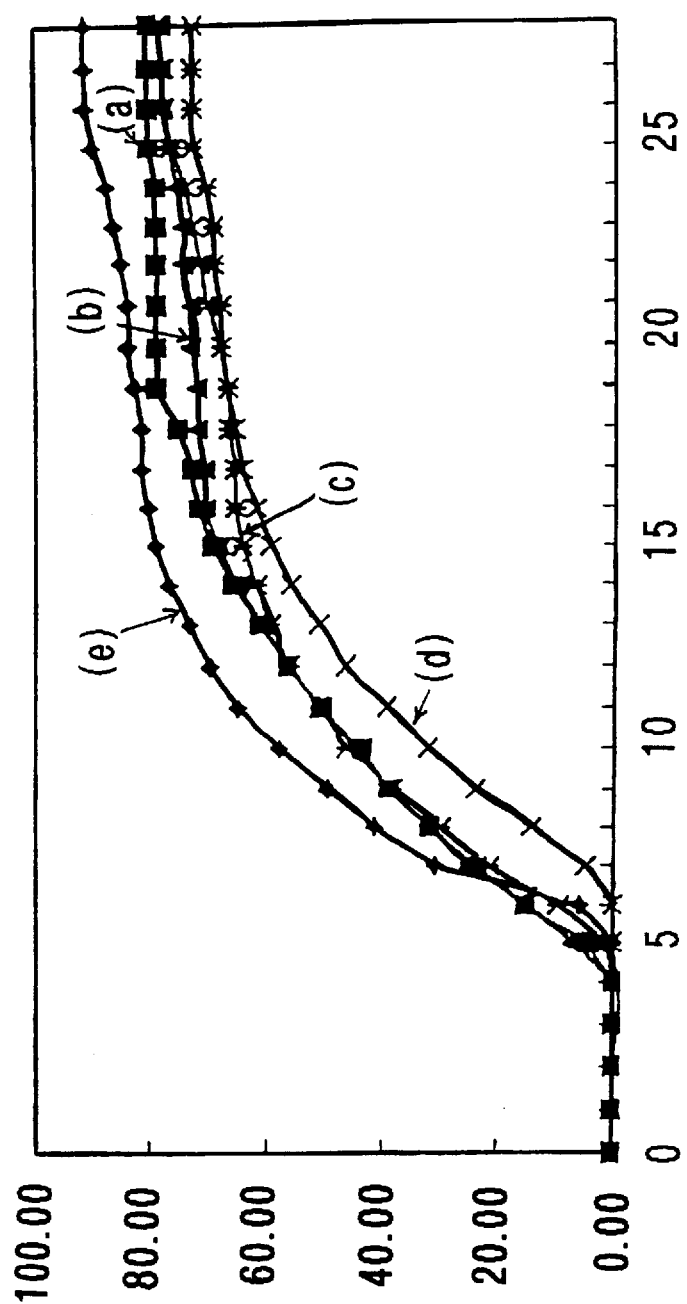
FIG. 1 shows the biodegradability measurement results of Examples 7 and 9 and Comparative example 4.

I claim:

1. A crosslinkable polylactone-based composition comprising 100 parts by weight of polylactone (A) having a number average molecular weight of 10,000 to 300,000 and 0.1 to 30 parts by weight of a crosslinkable monomer (B), wherein the crosslinkable polylactone-based composition is crosslinked by irradiating active energy radiation or by heating at 120° to 250° C. so as to obtain a crosslinked molded article whose recovery ratio is not less than 80%.

2. A crosslinkable polylactone-based composition as set forth in claim 1, characterized by selecting the crosslinkable monomer (B) from the group consisting of a polyfunctional acrylic monomer ($B_1$), a mixed monomer ($B_2$) of a polyfunctional isocyanate and a polyfunctional alcohol, and a mixed monomer ($B_3$) of a polyfunctional isocyanate and a polyfunctional amine.

3. A production method of a polylactone-based crosslinked molded article as set forth in claim 1 in which crosslinking is carried out at a temperature of 120° to 250° C.

4. A polylactone-based crosslinked molded article obtained by crosslinking by irradiating active energy radiation or by heating after melting and molding at a temperature where crosslinking of the crosslinkable polylactone-based composition as set forth in claims 1 or 2 will not occur.

5. A polylactone-based crosslinked molded article described in claim 4 whose recovery ratio is not less than 80%.

6. A polylactone-based crosslinked molded article as set forth in claim 4 which is a sheet for fixing a patient in radiation therapy.

7. A polylactone-based crosslinked molded article as set forth in claim 4 which is a material for transcribing a shape of wig.

8. A polylactone-based crosslinked molded article as set forth in claim 4 which is a material for transcribing a shape of teeth.

9. A polylactone-based crosslinked molded article as set forth in claim 4 which is a tape or sheet for gypsum.

10. A polylactone-based crosslinked molded article as set forth in claim 4 which is a biodegradability disposable-type molded article having biodegradability.

11. A curable polylactone based composition comprising a polylactone or a polylactone composition (X) containing 20 to 100% by weight of polylactone (C) having a number average molecular weight of 10,000 to 200,000 and hydroxyl group moles per 1 g of 1×10–5 to 5×10–4 moles and 0 to 80% by weight of a polyvalent alcohol (D) having a number average molecular weight of less than 10,000 (the total of (C) and (D) is 100% by weight.), and one or more curing agent(s) (Y) selected from poly functional isocyanates, poly functional epoxides, poly functional carboxylic acids and melamine compounds, wherein the curable polylactone based composition is cured by heating at 100° to 250° C. so that a chloroform-insoluble gel content of the cured product is not less than 5%.

12. A production method of a cured polylactone-based molded article characterized by molding the curable polylactone-based composition as set forth in claim 11 the temperature range of 100° to 250° C.

13. A production method of a cured polylactone-based molded article characterized by molding the curable polylactone-based composition as set forth in claim 11 with curing in the temperature range of 100° to 250° C.

14. A production method of a cured polylactone-based molded article characterized by molding the curable polylactone-based composition as set forth in claim 11 in the temperature range of 100° to 250° C. without curing or with partial curing, and by reheating the obtained uncured molded article at 100° to 250° C.

15. A production method of the cured polylactone-based molded article as set forth in claim 13 where the molded article is a sheet by compression molding or a bottle by vacuum molding.

16. A production method of a cured polylactone-based molded article as set forth in claim 14 where the molded article is a film by inflation molding or T-die molding, or a bottle by blow molding, and a support to prevent the above-mentioned films or bottles from mutually fused adhesion is used in reheating.

17. A production method of a cured polylactone-based molded article characterized by reheating the cured polylactone-based molded article obtained by the production method of the cured polylactone-based molded article as set forth in claim 12 in the temperature range of 100° to 250° C.

18. A cured polylactone-based molded article obtained by molding the cured polylactone-based composition as set forth in claim 11 in the temperature range of 100° to 250° C.

19. A cured polylactone-based molded article obtained by molding the curable polylactone-based composition as set forth in claim 11, and reheating the obtained molded article in the temperature range of 100° to 250° C.

20. A cured polylactone-based molded article as set forth in claim 18 characterized in that the chloroform-insoluble gel content is over 30% by weight.

21. A cured polylactone-based molded article as set forth in claim 19 characterized in that the chloroform-insoluble gel content is over 30% by weight.

22. A cured polylactone-based molded article as set forth in claim 18 whose recovery ratio is not less than 60%.

23. A cured polylactone-based molded article as set forth in claim 18 which is a sheet for fixing a patient in radiation therapy.

24. A cured polylactone-based molded article as set forth in claim 18 which is a material for transcribing a shape of wig.

25. A cured polylactone-based molded article as set forth in claim 18 which is a material for transcribing a shape of teeth.

26. A cured polylactone-based molded article as set forth in claim 18 which is a tape or sheet for gypsum.

* * * * *

UNITED STATES PATENT AND TRADEMARK OFFICE
CERTIFICATE OF CORRECTION

PATENT NO. : 5,889,140
DATED : March 30, 1999
INVENTOR(S) : Kazushi Wanatabe It is certified that error appears in the above-identified patent and that said Letters Patent is hereby corrected as shown below:

Renumber Columns 21 through 30 as Columns 11 through 20, respectively

Signed and Sealed this

Seventh Day of September, 1999

Attest:

Q. TODD DICKINSON

Attesting Officer

Acting Commissioner of Patents and Trademarks